United States Patent
Kavsak et al.

(10) Patent No.: US 11,789,028 B2
(45) Date of Patent: Oct. 17, 2023

(54) METHOD AND PANEL FOR DETERMINING ACUTE KIDNEY INJURY

(71) Applicants: MCMASTER UNIVERSITY, Hamilton (CA); Yale University, New Haven, CT (US)

(72) Inventors: Peter Kavsak, Hamilton (CA); Richard Whitlock, Hamilton (CA); John Eikelboom, Hamilton (CA); Chirag R. Parikh, Wallingford, CT (US)

(73) Assignee: MCMASTER UNIVERSITY, Hamilton (CA)

( * ) Notice: Subject to any disclaimer, the term of this patent is extended or adjusted under 35 U.S.C. 154(b) by 489 days.

(21) Appl. No.: 15/459,463

(22) Filed: Mar. 15, 2017

(65) Prior Publication Data

US 2017/0248611 A1    Aug. 31, 2017

Related U.S. Application Data

(63) Continuation-in-part of application No. PCT/CA2015/050892, filed on Sep. 15, 2015.

(60) Provisional application No. 62/050,403, filed on Sep. 15, 2014.

(51) Int. Cl.
*G01N 33/68* (2006.01)
*C12Q 1/6883* (2018.01)

(52) U.S. Cl.
CPC ....... *G01N 33/6893* (2013.01); *C12Q 1/6883* (2013.01); *G01N 33/6869* (2013.01); *C12Q 2600/158* (2013.01); *G01N 2333/47* (2013.01); *G01N 2333/5412* (2013.01); *G01N 2333/5428* (2013.01); *G01N 2800/347* (2013.01); *G01N 2800/50* (2013.01)

(58) Field of Classification Search
CPC ........... G01N 33/6869; G01N 33/6893; G01N 2333/5412; G01N 2333/5428; G01N 2800/50; G01N 2800/347; G01N 2333/47
See application file for complete search history.

(56) References Cited

U.S. PATENT DOCUMENTS

| | | |
|---|---|---|
| 2011/0059537 A1 | 3/2011 | Liangos et al. |
| 2014/0187652 A1 | 7/2014 | Heudig et al. |

FOREIGN PATENT DOCUMENTS

| | | |
|---|---|---|
| CA | 2790785 A1 | 9/2011 |
| WO | 2011/035323 A1 | 3/2011 |

OTHER PUBLICATIONS

Haase, M, et al. Sodium bicarbonate to prevent increases in serum creatinine after cardiac surgery: a pilot double-blind, randomized controlled trial. Crit. Care Med., 2009, 37(1):39-47.*
Haase et al. Crit. Care Med., 2009, 37(1):39-47 (Year: 2009).*
Greenberg et al. Interleukin-6 and interleukin-10 as acute kidney injury biomarkers in pediatric cardiac surgery. Pediatr Nephrol (2015) 30:1519-1527 (Year: 2015).*
Miklaszewska et al. Serum Interleukin 6 levels as an early Adv. Clin. Exp. Med., May-Jun. 2013, 22(3):377-386 (Year: 2013).*
Bucholz et al. Cardiac Biomarkers and Acute Kidney Injury After Cardiac Surgery. Pediatrics, Apr. 2015; 135(5): e945-e956 (Year: 2015).*
Haase et al. Sodium bicarbonate to prevent increases in serum vreatinine after surgery: a pilot double-blind, randomized controlled trial. Crit. Care Med., 2009, 37(1):39-47 (Year: 2009).*
Miklaszewska et al. Adv. Clin. Exp. Med., May-Jun. 2013, 22(3):377-386 (Year: 2013).*
Bucholz et al. Pediatrics, Apr. 2015; 135(5): e945-e956 (Year: 2015).*
EP 15 84 1676, Supplemental European Search Report, Date of Completion, Jan. 26, 2018.
Pelsers, 2009, Ned Tijdschr Klin Chem Labgeneesk, 34, 4, 250-251.
PCT/CA2015/050892, Written Opinion of the ISA, Nov. 10, 2015.
Oezkur, et al. (2014) BMC Cardiovascular Disorders 2014, 14:117.
Liu, et al. (2009) Critical Care 2009; 13(4):R104.
Denne, et al. (2010) Critical Care. 2010; 14(5):R181.
Miklaszewska, et al. (2013) Adv. Clin. Exp. Med. 22(3):377-86.
Yilmaz, et al. (2014) Clin. J. Am. Soc. Nephrol. Jul. 2014; 9(7):1207-16.
Taniguchi (1999) Am. J. Emerg. Med. Oct. 1999; 17(6):548-51.
Al-Hadi, et al. (2009) Sultan Qaboos Univ. Med. J. Dec. 2009; 9(3):311-314.
Zakrzewski, et al. (2010) Kardiol Pol. May 2010; 68(5):530-536.
PCT/CA2015/050892, Int'l Search Report, dated Nov. 10, 2015.
John Hopkins Medicine, Health, Anesthesia, Types of Anesthesia, access Oct. 15, 2019.
La Paz Regional Hospital & Clinics, the Five Stages of Your Surgery, accessed Oct. 15, 2019.
Whitlock, VerywellHealth, Overview of the Perioperative Phases of Surgery, accessed Sep. 22, 2020.
Kahn, et al. Blood-sampling collection prior to surgery may have a significant influence upon biomarker concentrations measured, Clinical Proteomics, 12:19, 2015.
Meisner, et al. (2018) "Development of biomarker combinations for postoperative acute kidney injury via Bayesian model selection in a multicenter cohort study" Biomark Res. 6:3.

(Continued)

*Primary Examiner* — Vanessa L. Ford
*Assistant Examiner* — Sandra Dillahunt
(74) *Attorney, Agent, or Firm* — Milstein Zhang & Wu LLC

(57) ABSTRACT

A method for determining the risk of acute kidney injury (AKI) in a mammal following cardiac surgery is provided. The method comprises determining the sample value of IL-6 or hFABP concentration, or the ratio of IL-6 to IL-10, in a biological sample from the mammal, either prior to cardiac surgery or within 6 hours following surgery; comparing the sample value to a corresponding reference value; and determining that the mammal is at risk of acute kidney injury following cardiac surgery if the sample value is greater than the corresponding reference value.

10 Claims, 15 Drawing Sheets

(56) References Cited

OTHER PUBLICATIONS

Lane, et al. (2018) "Evaluation of Urinary Renal Biomarkers for Early Prediction of Acute Kidney Injury Following Partial Nephrectomy: a Feasibility Study" Eur Urol Focus. Nov. 10, 2018. pii: S2405-4569(18)30318-3.

* cited by examiner

Figure 5.

| | Unadjusted | | Adjusted[†] | |
|---|---|---|---|---|
| | OR (95% CI) | p-value | OR (95% CI) | p-value |
| Pre-operative Biomarkers | | | | |
| FABP (n=98) | 2.72 (1.48, 5.01) | <0.01 | 2.76 (1.27, 6.03) | 0.01 |
| First Post-operative Biomarkers | | | | |
| FABP (n=105) | 1.29 (0.86, 1.92) | 0.21 | 1.07 (0.63, 1.82) | 0.80 |

Figure 6.

| | Unadjusted AUC (95% CI) | Adjusted AUC (95% CI) |
|---|---|---|
| | Biomarker only | Biomarker + clinical model |
| Preoperative Biomarkers | | |
| Clinical Model* | -- | 0.74 (0.64, 0.83) |
| FABP | 0.70 (0.60, 0.81) | 0.78 (0.68, 0.87) |
| Postoperative Biomarkers | | |
| Clinical Model† | -- | 0.74 (0.64, 0.84) |
| FABP | 0.56 (0.45, 0.67) | 0.73 (0.63, 0.83) |

Figure 7.

| | NRI | | IDI | |
|---|---|---|---|---|
| | Estimate (SE) | p-value | Estimate (SE) | p-value |
| Preoperative Biomarkers | | | | |
| FABP | 0.42 (0.20) | 0.04 | 0.07 (0.03) | 0.01 |
| Postoperative Biomarkers | | | | |
| FABP | 0.14 (0.20) | 0.49 | <0.01 (0.01) | 0.82 |

Figure 10.

| Biomarker Tertile | Range | Unadjusted | | Adjusted* | |
|---|---|---|---|---|---|
| | | OR (95% CI) | p-value | OR (95% CI) | p-value |
| IL-6 pre-op | | | | | |
| T1 | (0.6 - 0.6) | 1.0 (referent) | 0.03 | 1.0 (referent) | 0.02 |
| T2 | (1.4 - 2.2) | 1.5 (0.3, 9.5) | | 1.2 (0.1, 11) | |
| T3 | (2.2 - 76.8) | 5.4 (1.5, 20) | | 7.9 (1.7, 37) | |
| IL-6 day 1 | | | | | |
| T1 | (17.9 - 63.4) | 1.0 (referent) | 0.7 | 1.0 (referent) | 0.4 |
| T2 | (63.4 - 126.7) | 1.4 (0.4, 4.7) | | 1.7 (0.5, 6.2) | |
| T3 | (135 - 313.7) | 1.7 (0.5, 5.3) | | 2.5 (0.7, 8.9) | |
| IL-6 day 3 | | | | | |
| T1 | (0.6 - 22.5) | 1.0 (referent) | 0.4 | 1.0 (referent) | 0.2 |
| T2 | (22.7 - 63.9) | 0.9 (0.3, 3.4) | | 0.3 (0.1, 1.5) | |
| T3 | (65.7 - 683) | 2.0 (0.6, 6.4) | | 1.0 (0.2, 3.8) | |
| IL-10 pre-op† | | | | | |
| T1 | (0.9 - 0.9) | 1.0 (referent) | 0.7 | 1.0 (referent) | 0.4 |
| T2 | (1.3 - 21.6) | 1.2 (0.4, 4.4) | | 0.4 (0.1, 3.0) | |
| IL-10 day 1 | | | | | |
| T1 | (3.1 - 70.3) | 1.0 (referent) | 0.1 | 1.0 (referent) | 0.05 |
| T2 | (71.2 - 110.2) | 3.9 (1.1, 14) | | 4.1 (1.1, 16.1) | |
| T3 | (112.8 - 545.2) | 1.9 (0.5, 7.1) | | 1.2 (0.3, 5.2) | |
| IL-10 day 3‡ | | | | | |
| T1 | (0.9 - 0.9) | 1.0 (referent) | 0.02 | 1.0 (referent) | 0.1 |
| T2 | (1.4 - 59.2) | 3.8 (1.3, 11) | | 3.1 (0.9, 10) | |

Figure 11.

| Biomarker | AKI n (%) | Unadjusted OR (95% CI) | Adjusted OR (95% CI) |
|---|---|---|---|
| IL-6 (pg/mL) | | | |
| T1 (0.6-1.9) | 8 (2.6%) | 1.00 (referent) | 1.00 (referent) |
| T2 (2.0-5.2) | 8 (2.6%) | 1.01 (0.37, 2.72) | 1.09 (0.39, 3.08) |
| T3 (5.2-633) | 17 (5.5%) | 2.20 (0.93, 5.17) | 2.17 (0.84, 5.63) |
| IL-10 (pg/mL) | | | |
| T1 (0.9) | 28 (3.4%) | 1.00 (referent) | 1.00 (referent) |
| T2 (1.5-168) | 3 (3.2%) | 0.93 (0.28, 3.10) | 0.96 (0.26, 3.61) |
| IL-6:IL-10 ratio | | | |
| T1 (0.03, 1.7) | 5 (1.7%) | 1.00 (referent) | 1.00 (referent) |
| T2 (1.7, 4.7) | 10 (3.3%) | 2.03 (0.69, 6.00) | 2.35 (0.76, 7.24) |
| T3 (4.7, 386) | 16 (5.3%) | 3.31 (1.20, 9.16) | 3.19 (1.06, 9.56) |

Figure 14.

| Biomarker | Time point | Tertiles | | | n (%) | Unadjusted | | Odds Ratio Model 1 | | Model 2 | |
|---|---|---|---|---|---|---|---|---|---|---|---|
| | | Tertile | n | range | | OR (95% CI) | pvalue | OR (95% CI) | pvalue | OR (95% CI) | pvalue |
| FABP | Pre-op | log | 944 | | 34 (3.6%) | 2.124 (1.203, 3.749) | 0.0094 | 2.126 (0.939, 4.813) | 0.0705 | | |
| | | T1 | 314 | (0.4-3.19) | 8 (2.5%) | 1.0 (referent) | NA | 1.0 (referent) | NA | 1.0 (referent) | NA |
| | | T2 | 315 | (3.2-5.14) | 7 (2.2%) | 0.869 (0.311, 2.427) | 0.7892 | 0.839 (0.287, 2.453) | 0.7484 | | |
| | | T3 | 315 | (5.15-64.03) | 19 (6.0%) | 2.455 (1.059, 5.695) | 0.0364 | 2.514 (0.858, 7.362) | 0.0928 | | |
| | Day 1 0-6 Hours | log | 955 | | 37 (3.9%) | 4.777 (2.901, 7.866) | <0.0001 | 5.388 (2.872, 10.108) | <0.0001 | 3.741 (1.903, 7.356) | 0.3549 |
| | | T1 | 318 | (2.15-23.99) | 4 (1.3%) | 1.0 (referent) | NA | 1.0 (referent) | NA | 1.0 (referent) | NA |
| | | T2 | 319 | (24.09-40.79) | 7 (2.2%) | 1.761 (0.51, 6.076) | 0.3704 | 1.488 (0.421, 5.254) | 0.5368 | 1.116 (0.293, 4.259) | 0.9659 |
| | | T3 | 318 | (40.8-141) | 26 (8.2%) | 6.99 (2.41, 20.269) | 0.0003 | 5.182 (1.6, 16.784) | 0.0061 | 2.774 (0.781, 9.858) | 0.7613 |
| | Peak | log | 957 | | 37 (3.9%) | 7.746 (4.315, 13.905) | <0.0001 | 8.371 (4.296, 16.311) | <0.0001 | 5.175 (1.91, 14.021) | 0.2507 |
| | | T1 | 319 | (2.15-25.51) | 4 (1.3%) | 1.0 (referent) | NA | 1.0 (referent) | NA | 1.0 (referent) | NA |
| | | T2 | 319 | (25.64-44.71) | 2 (0.6%) | 0.497 (0.09, 2.732) | 0.4212 | 0.344 (0.06, 1.961) | 0.2297 | 0.349 (0.034, 3.536) | 0.8651 |
| | | T3 | 319 | (44.79-141) | 31 (9.7%) | 8.477 (2.956, 24.307) | <0.0001 | 6.016 (1.908, 18.971) | 0.0022 | 2.723 (0.477, 15.559) | 0.6158 |

Figure 15.

| | Time point | Tertile | range | n (%) | Unadjusted OR (95% CI) | Model 1 OR (95% CI) | Model 2 OR (95% CI) | AUC | Roc Curve cut point | Sens. | Spec. |
|---|---|---|---|---|---|---|---|---|---|---|---|
| hFABP | pre | T1 n=314 | (0.4-3.19) | 8 (2.5%) | 1.0 (referent) | 1.0 (referent) | 1.0 (referent) | 0.63 (0.06) | 6.2 | 0.53 | 0.81 |
| | | T2 n=315 | (3.2-5.14) | 7 (2.2%) | 0.869 (0.311, 2.427) | 0.839 (0.287, 2.453) | | | 0.4 | 1 | 0 |
| | | T3 n=315 | (5.15-64.03) | 19 (6.0%) | 2.455 (1.059, 5.695) | 2.514 (0.858, 7.362) | | | 3.2 | 0.76 | 0.34 |
| hFABP | Day 1 0-6 Hours | T1 n=318 | (2.15-23.99) | 4 (1.3%) | 1.0 (referent) | 1.0 (referent) | 1.0 (referent) | 0.77 (0.04) | 53.8 | 0.68 | 0.67 |
| | | T2 n=319 | (24.09-40.79) | 7 (2.2%) | 1.761 (0.51, 6.076) | 1.488 (0.421, 5.254) | 1.116 (0.293, 4.259) | | 2.2 | 1 | 0.81 |
| | | T3 n=318 | (40.8-141) | 26 (8.2%) | 6.99 (2.41, 20.269) | 5.182 (1.6, 16.784) | 2.774 (0.781, 9.858) | | 24.1 | 0.89 | 0.34 |
| IL-6 | pre | T1 n=309 | (0.6-1.94) | 8 (2.6%) | 1.0 (referent) | 1.0 (referent) | 1.0 (referent) | 0.39 (0.04) | 40.8 | 0.7 | 0.68 |
| | | T2 n=307 | (1.95-5.16) | 8 (2.6%) | 1.007 (0.373, 2.717) | 1.092 (0.387, 3.077) | | | 20.4 | 1 | 0.09 |
| | | T3 n=308 | (5.19-633.4) | 17 (5.5%) | 2.198 (0.934, 5.172) | 2.171 (0.838, 5.626) | | | 0.6 | 0.09 | 0.76 |
| IL-6 | Day 1 0-6 Hours | T1 n=318 | (6.21-111.1) | 4 (1.3%) | 1.0 (referent) | 1.0 (referent) | 1.0 (referent) | 0.71 (0.05) | 2 | 0.24 | 0.66 |
| | | T2 n=319 | (111.6-239.4) | 9 (2.8%) | 2.279 (0.695, 7.478) | 1.512 (0.435, 5.257) | 0.721 (0.183, 2.837) | | 5.2 | 0.48 | 0.33 |
| | | T3 n=318 | (241.3-791) | 24 (7.5%) | 6.408 (2.197, 18.689) | 2.99 (0.94, 9.511) | 1.855 (0.535, 6.431) | | 248.4 | 0.65 | 0.69 |
| IL-6/IL-10 ratio | pre | T1 n=302 | (0.03, 1.69) | 5 (1.7%) | 1.0 (referent) | 1.0 (referent) | 1.0 (referent) | 0.39 (0.05) | 6.2 | 1 | 0 |
| | | T2 n=303 | (1.72, 4.7) | 10 (3.3%) | 2.027 (0.685, 6.002) | 2.347 (0.76, 7.244) | | | 111.6 | 0.89 | 0.34 |
| | | T3 n=303 | (4.71, 386.33) | 16 (5.3%) | 3.311 (1.197, 9.156) | 3.189 (1.064, 9.558) | | | 241.3 | 0.65 | 0.68 |
| IL-6/IL-10 ratio | Day 1 0-6 Hours | T1 n=318 | (0.07, 2.19) | 12 (3.8%) | 1.0 (referent) | 1.0 (referent) | 1.0 (referent) | 0.55 (0.05) | 22.7 | 1 | 0.06 |
| | | T2 n=319 | (2.19, 8.88) | 10 (3.1%) | 0.825 (0.351, 1.939) | 0.753 (0.307, 1.846) | 0.565 (0.205, 1.56) | | 0 | 0 | 1 |
| | | T3 n=318 | (8.91, 878.89) | 15 (4.7%) | 1.263 (0.581, 2.742) | 1.314 (0.532, 3.246) | 1.065 (0.389, 2.916) | | 1.7 | 0.16 | 0.66 |

METHOD AND PANEL FOR DETERMINING ACUTE KIDNEY INJURY

PRIORITY CLAIMS AND RELATED PATENT APPLICATIONS

This application claims the benefit of priority, under 35 U.S.C. § 120, from the US designation of International Application No. PCT/CA2015/050892, filed on Sep. 15, 2015, which claims benefit of priority from U.S. Provisional Application Ser. No. 62/050,403, filed on Sep. 15, 2014, the entire content of each of which is incorporated herein by reference in its entirety for all purposes.

FIELD OF THE INVENTION

The present invention relates generally to prognostic methods for risk of acute kidney injury, and to panels for use therewith, and more particularly relates to prognostic methods associated with the risk of developing acute kidney injury in children and adults following cardiac surgery.

BACKGROUND OF THE INVENTION

Cardiac surgery can give rise to various complications resulting in adverse patient outcomes. Acute kidney injury (AKI) is an especially common and serious outcome.

Patients undergoing cardiac surgery, especially children, may exhibit a pronounced inflammatory response with the extent of myocardial injury. Inflammation is recognized as an important pathophysiologic process leading to acute kidney injury (AKI) as is injury to the myocardium. Often, it is diagnosed on the basis of blood tests for substances normally eliminated by the kidney: urea and creatinine. Both tests have their disadvantages. For instance, it takes about 24 hours for the creatinine level to rise, even if both kidneys have ceased to function. A number of alternative markers has been proposed (such as NGAL, KIM-1, IL18 and cystatin C), but none are currently established enough to replace creatinine as a marker of renal function.

It would be desirable, thus, to determine whether or not the inflammation process and/or myocardial injury status may be useful to predict risk of an adverse patient outcome following cardiac surgery, for example, risk of AKI.

SUMMARY OF THE INVENTION

It has now been determined that the expression of certain compounds, pre- or post-operatively, including certain inflammatory compounds, are useful to predict risk of AKI following cardiac surgery in both children and adults.

In one aspect, a method for determining the risk of acute kidney injury in a mammal following cardiac surgery is provided. The method comprises measuring the concentration of one or more biomarkers selected from the group of IL-6, hFABP (heart-type FABP) and IL-10 in a biological sample from the mammal, either prior to cardiac surgery or within 6 hours following surgery; comparing the concentration of the biomarker(s) with that of a corresponding control or reference value; and determining that the mammal is at risk of acute kidney injury following cardiac surgery if the concentration of the biomarker(s) is equal to or greater than the corresponding reference value.

In another aspect a method of determining risk of AKI in a mammal and treating the mammal is provided. The method comprises measuring the concentration of one or more biomarkers selected from the group of IL-6, hFABP (heart-type FABP) and IL-10 in a biological sample from the mammal, either prior to cardiac surgery or within 6 hours following surgery; comparing the concentration of the biomarker(s) with that of a corresponding control or reference value; determining that the mammal is at risk of acute kidney injury following cardiac surgery if the concentration of the biomarker(s) is equal to or greater than the corresponding reference value; and treating the mammal to maintain volume homeostasis and correct biochemical abnormalities.

In another aspect, a kit useful to determine risk of AKI in a mammal is provided. The kit comprises a biomarker-specific reactant for each of IL-6, IL-10 and hFABP.

These and other aspects of the invention will become apparent by reference to the detailed description and figures which follow.

BRIEF DESCRIPTION OF THE FIGURES

FIG. 5 graphically illustrates logistic regression models for prediction development of AKI using pre- and post-operative biomarker values (all values of biomarkers have been log transformed). †Preoperative biomarker models adjusted for age (years), site, and preoperative eGFR percentile. Post-operative biomarker models adjusted for age (years), site, CPB time>120 min, and preoperative eGFR;

FIG. 6 illustrates a ROC Analysis. Area under the curve (AUC) for prediction of AKI *Preoperative clinical models is adjusted for age (years), site, and preoperative eGFR percentile. †Post-operative clinical models is adjusted for age (years), site, CPB time>120 min, and preoperative eGFR percentile;

FIG. 7 is a comparison of models with cardiac markers to clinical model using NRI/IDI;

FIG. 10 provides logistic regression models for development of severe acute kidney injury. * Adjusted for age, gender, race, surgical site. † IL-10 pre-op were undetectable in 78% of the sample and are in T1. ‡ IL-10 day 3 were undetectable in 68% of the sample and are in T1;

FIG. 11 shows tertiles of preoperative inflammatory biomarkers and risk of AKI. Adjusted for age, sex, white race, non-elective surgery, pre-op eGFR, diabetes, hypertension, centre, congestive heart failure, myocardial infarction, pre-op urine albumin to creatinine ratio, and type of surgery; OR=odds ratio, CI=confidence interval. Number of patients per Tertile: IL-6 T1 n=309, T2 n=307 T3 n=308; IL-10 T1 n=814, T2 n=94; IL-6:IL-10 ratio T1 n=302, T2 n=303, T3 n=303;

FIG. 14 shows the association between biomarkers and severe AKI. For Preoperative Biomarkers. Model 1: adjusted for age (per year), sex, white race, non-elective surgery, diabetes, hypertension, centre, congestive heart failure (CHF), myocardial infarction (MI), preoperative urine albumin to creatinine ratio, and type of surgery (CABG or valve vs. all others). For day 10.6 hour Biomarkers. i) Model 1: adjusted for age (per year), sex, white race, non-elective surgery, diabetes, hypertension, centre, congestive heart failure (CHF), myocardial infarction (MI), preoperative urine albumin to creatinine ratio, and type of surgery (CABG or valve vs. all others) ii) Model 2: model 1+change in serum creatinine day 10 6 hours from preoperative. For Peak Biomarkers. Model 1: adjusted for age (per year), sex, white race, non-elective surgery, diabetes, hypertension, centre, congestive heart failure (CHF), myocardial infarction (MI), preoperative urine albumin to creatinine ratio, and type of surgery (CABG or valve vs. all others). Model 2: model 1+change in serum creatinine from preoperative; and FIG. 15 shows biomarker associations with severe AKI. The Odds Ratio for hFABP, IL-6 and IL-6/IL-10 ratio. Model 1: Adjusted for Age (per year), sex, white race, non-elective surgery, diabetes, hypertension, centre, congestive heart failure (CHF), myocardial infarction (MI), pre-op urine albumin to creatinine ratio, and type of surgery (CABG or valve vs. all others). Post-op biomarkers are also adjusted for CPB time>120 minutes. Model 2: Model 1+change in serum creatinine day 1 0-hours from-pre-op.

DETAILED DESCRIPTION OF THE INVENTION

Figure 1:
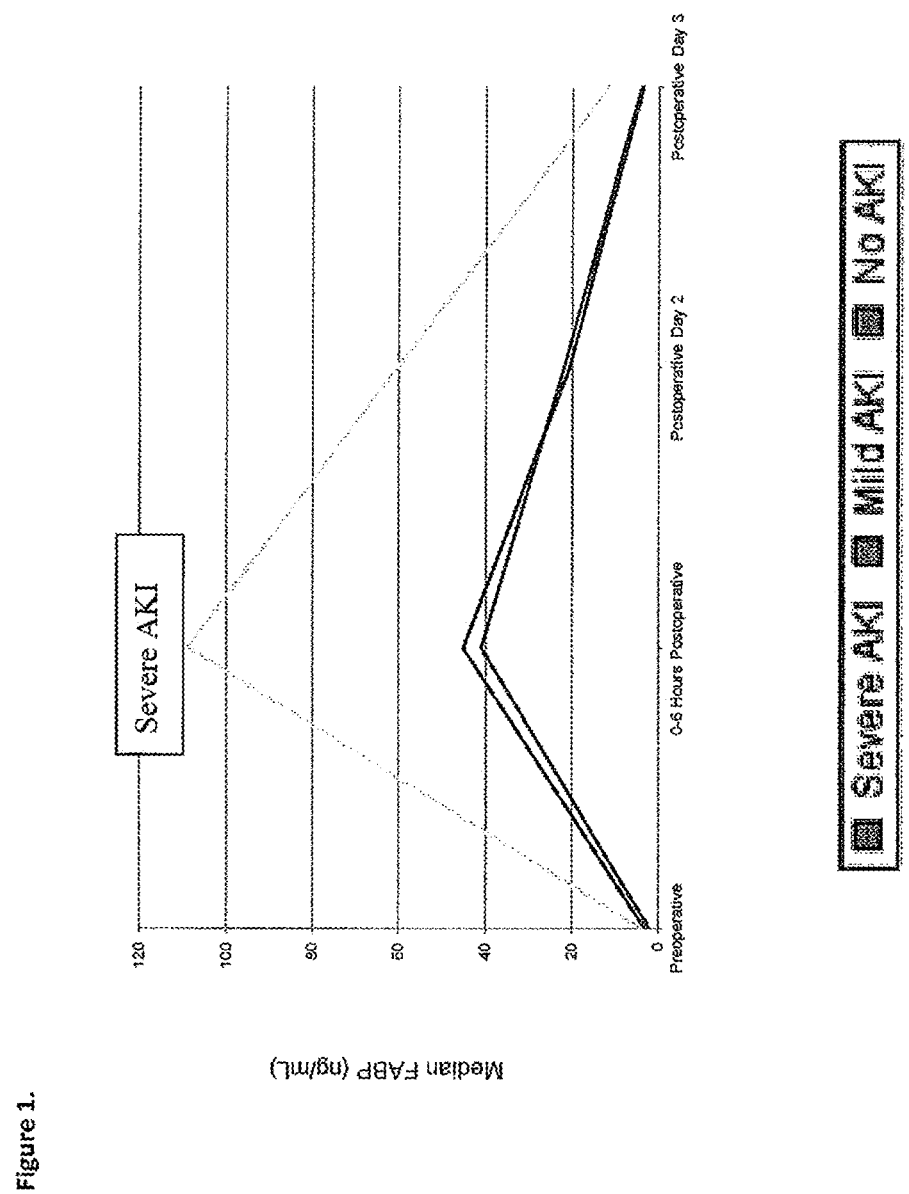
FIG. 1 illustrates the median biomarker values by AKI group collected preoperatively and 0-6 hours, 2 days, and 3 days after surgery.

A method for determining the risk of acute kidney injury in a mammal following cardiac surgery is provided, optionally including treatment of the mammal. The method comprises measuring the concentration of one or more biomarkers selected from the group of IL-6, hFABP and IL-10 in a biological sample from the mammal, either prior to cardiac surgery or within 6 hours following surgery; comparing the concentration of the biomarker(s) with that of a corresponding reference value; and determining that the mammal is at risk of acute kidney injury following cardiac surgery if the concentration of the biomarker(s) is equal to or greater than the corresponding reference value.

Acute kidney injury (AKI), previously called acute renal failure (ARF), refers to loss of kidney function that develops within 6 days, e.g. following cardiac surgery. Kidney function may be assessed by glomerular filtration rate (GFR), i.e. the flow rate of filtered fluid through the kidney (for example, by the RIFLE class system, a GFR decrease >25% from baseline classifies risk, while injury is defined by a GFR>50% from baseline, as described in Nature Reviews Nephrology 7, 201-208; April 2011), or by creatinine clearance rate ($C_{Cr}$ or CrCl), i.e. the volume of blood plasma that is cleared of creatinine per unit time. Thus, loss of kidney function may be determined by an increase in blood levels of creatinine, e.g. a 50% or greater increase in creatinine concentrations.

The term "IL-6" refers to the mammalian cytokine, Interleukin-6, and encompasses both human IL-6, as depicted by NCBI accession no. NP000591, as well as functionally equivalent IL-6 of other mammalian species, for example, mouse IL-6 as depicted NCBI accession no. NP112445, and any functionally equivalent isoforms of an IL-6. Also encompassed are IL-6-like compounds such as a gp130 cytokine family member (e.g. gp130, LIF-R (NP002301), OSM-R (Q99650), and G-CSF-R (NP000751), or a soluble gp130 receptor (e.g., soluble IL-6 receptor). IL-6-like compounds are related to IL-6 such that an increase or decrease in the level of these compounds is indicative of a corresponding increase or decrease in IL-6 level.

The term "IL-10" refers to mammalian Interleukin-10. IL-10 is also known as human cytokine synthesis inhibitory factor (CSIF) and is an anti-inflammatory cytokine. "IL-10" encompasses both human IL-10 as depicted by NCBI accession no. NP000563, as well as functionally equivalent IL-10 of other mammalian species, for example, mouse IL-10 as depicted by NCBI accession no. NP034678, and functionally equivalent isoforms of an IL-10. Also encompassed are IL-10-like compounds such as cytokines belonging to the extended IL-10 superfamily (e.g. IL-10, IL-19, IL-20, IL-22, IL-24, IL-26, IL-28, and IL-29) or a receptor thereof. IL-10-like compounds are related to IL-10 such that an increase or decrease in the level of these compounds is indicative of a corresponding increase or decrease in IL-10 level.

The term "hFABP" or "heart-type fatty acid binding protein" refers to a small cytoplasmic protein (15 kDa) released from cardiac myocytes following an ischemic episode. It is encoded by the FABP3 gene in humans. The term hFABP is used herein to encompass mammalian, including human hFABP as depicted by NCBI accession no. NP004093, as well as functionally equivalent hFABP from other mammalian species, for example, mouse hFABP as depicted by NCBI accession no. NP034304, and any functionally equivalent isoforms of an hFABP.

The term "functionally equivalent" as used herein is meant to refer to forms of a compound, e.g. such as IL-6, IL-10 and hFABP, including all mammalian forms from different species, and isoforms, variants or mutants of any of these, that possess the same or similar function and/or activity, e.g. which retain at least about 50% of the activity of a native mammalian form of IL-6, IL-10 or hFABP, and preferably retain at least about 60%, 70%, 80%, 90% or more activity of the native mammalian form.

The term "mammal" is used herein to refer to both human and non-human mammals including domestic animals, e.g. cats, dogs and the like, livestock and undomesticated animals.

In a first step of the method, a biological sample is obtained from a mammal either prior to cardiac surgery (e.g. within about 2-4 months prior to surgery, preferably within 60 days prior to surgery or less), or following cardiac surgery, e.g. within 3 days post surgery, and preferably within 24 hours, e.g. within 6 hours post-surgery. The term "cardiac surgery" is meant to encompass any surgery involving the heart, including but not limited to, cardiopulmonary bi-pass, septal defect repair, inflow/outflow tract or valve procedure, heart valve repair or replacement, surgery to place ventricular assist devices or total artificial hearts, aneurysm repair, arrhythmia treatment, and the like.

The term "biological sample" is meant to encompass any mammalian sample that contains one or more of the biomarkers, IL-6, IL-10 or hFABP and/or related proteins, e.g. related proteins, such as those described above, that may be indicative of the level or concentration of one of IL-6, IL-10 or hFABP in the sample. Suitable biological samples include, for example, blood, serum, plasma and urine. The sample is obtained from the mammal in a manner well established in the art.

Once a suitable biological sample is obtained, it is analyzed for the level of one or more of the biomarkers, IL-6, IL-10 or hFABP. If appropriate, a related protein indicative of the level of one of IL-6, IL-10 or hFABP may be analyzed in place of any one or more of IL-6, IL-10 or hFABP. This determination may be accomplished using various methods established in the art, for example, by Enzyme Linked ImmunoSorbent Assays (ELISAs) or Enzyme ImmunoAssay (EIA). In this assay, the biomarker to be analyzed is complexed with a reactant specific for the biomarker, such as an antibody which is linked (either before or following formation of the complex) to an indicator, such as an enzyme. Detection may then be accomplished by incubating this enzyme-complex with a substrate for the enzyme, for example, that produces a detectable product. The indicator may be linked directly to the reactant (e.g. antibody) or via a linker, such as a secondary antibody that recognizes the first or primary antibody, or a protein such as streptavidin, if the primary antibody is biotin-labeled. Examples of suitable enzymes include, but are not limited to, horseradish peroxidase (HRP), alkaline phosphatase (AP), β-galactosidase, acetylcholinesterase and catalase. A large selection of substrates is available for performing the ELISA with an HRP or AP conjugate. Useful substrates depend on the level of detection required and the detection instrumentation used, e.g. spectrophotometer, fluorometer or luminometer.

A convenient method by which multiple biomarker levels in a sample may be determined utilizes, for example, biochip array technology. Generally, biochip arrays provide a means to simultaneously determine the level of multiple biomarkers in a sample. These arrays may, in one embodiment, be based on ELISA principles of sandwich or competitive immunoassays and, thus, the biochip provides a reaction platform including biomarker-specific antibodies attached at pre-defined sites on the surface. An amount of biological sample in the range of about 80-120 µl is generally used to determine biomarker levels utilizing a biochip.

Other methods of detecting the subject proteins may also be utilized as would be appreciated by one of skill in the art, including for example, mass spectrometry, gel electrophoresis as used in Western Blot techniques and other methods used in clinical chemistry.

In another embodiment, the expression level of protein biomarkers in a biological sample from a mammal may be determined based on the levels of nucleic acid (i.e. DNA, mRNA transcript or miRNA) encoding or associated with the target protein biomarkers in the biological sample. Methods of determining DNA or mRNA levels are known in the art, and include, for example, PCR-based techniques (such as RT-PCR), microarrays, the Nanospring nCounter gene expression system using color-coded probe pairs and Northern or Southern blotting techniques which generally include the application of gel electrophoresis to isolate the target nucleic acid, followed by hybridization with specific labeled probes. Probes for use in these methods can be readily designed based on the known sequences of genes encoding the protein biomarkers, as well as the known amino acid sequence of the target biomarkers. For example, the mRNA sequence for human IL-6 is depicted by NCBI accession no. NM_000600.3, the mRNA sequence for human IL-10 is depicted by NCBI accession no. NM_000572.2, and the mRNA sequence for human hFABP is depicted by NCBI accession no. NM_004102.3. Suitable labels for such probes are well-known, and include, for example, fluorescent, chemiluminescent and radioactive labels.

A determination of a concentration or level of IL-6, IL-6:IL-10 ratio or hFABP levels in the sample, pre- or post-operatively, that is equal to or greater than a corresponding reference value (e.g. equal to or greater than about the 67% percentile (or top tertile) levels of IL-6, IL-6:IL-10 ratio or hFABP, respectively, in the relevant cardiac surgical population, e.g. population having the same or similar cardiac procedure) is indicative of risk of AKI following cardiac surgery. For example, the pre-operative reference concentration for hFABP may be at least about 3 ng/ml, and preferably 5 ng/ml or greater, e.g. 10-20 ng/ml, and the post-operative reference concentration (up to 6 hours post-op) for hFABP may be at least about 20 ng/ml, and preferably 30-40 ng/ml or greater; the pre-operative reference concentration for IL-6 may be at least about 2 µg/mL, and preferably 5 µg/mL or greater, and the post-operative concentration (up to 6 hours post-op) for IL-6 may be at least about 100 µg/ml, and preferably 200-240 µg/ml or greater; and the pre-operative reference ratio for IL-6:IL-10 may be at least about 1.8, and preferably at least 4.5 or greater, e.g. 20, 50, 100, or greater, and the post-operative reference ratio for IL-6:IL-10 (up to 6 hours post-op) may be at least about 2, and preferably at least about 8.5 or greater, e.g. 20, 50, 100 or greater. FIGS. 14 and 15 provide non-limiting example concentrations. Minimally, pre- or post-operative levels of IL-6, IL-6:IL-10 ratio, or hFABP equal to the reference value is sufficient to be indicative of risk of AKI. Increased levels of at least about 10%, preferably 20% or greater, e.g. 30%, 40%, 50% or greater, in the level of any of IL-6, IL-6:IL-10 ratio, or hFABP in a sample from a patient as compared to the reference value, is indicative of an increased risk of AKI. However, when the biomarkers are treated as continuous variables, preferably a combination of IL-6 and hFABP, and more preferably, a combination of IL-6:IL-10 and hFABP, is used to determine AKI risk in a patient sample.

The phrase "risk of AKI" refers to at least about a 20% increased chance of developing AKI (e.g. risk of AKI), preferably 30-40% chance of developing AKI (e.g. increased risk of AKI), or a 50% or greater chance of developing AKI (e.g. significantly increased risk of AKI). In this regard, the greater the increase in the concentration of the biomarker compared to the reference value, the greater the risk of AKI, and as above, increased levels of both IL-6 and hFABP compared to reference values results in an increased risk of AKI.

Determination in a patient of risk of AKI allows for appropriate patient management, including precautions to be taken and suitable treatments to be employed pre- and post-operatively. For example, in addressing AKI in a patient, or potential AKI, it is important to maintain volume homeostasis and correct biochemical abnormalities. Depending on the severity of AKI, dialysis may be required to maintain volume homeostasis and correct biochemical abnormalities. Dialysis is generally indicated for refractory hyperkalemia; volume overload; intractable acidosis; uremic encephalopathy, pericarditis, or pleuritis; and removal of certain toxins. Other treatments may include the following. Maintenance of fluid homeostasis may be achieved by intravenous fluid management. Fluid overload may be corrected with furosemide. Biochemical abnormalities are monitored and corrected as required. For example, since hyperkalemia in patients with AKI can be life-threatening, serum potassium levels may be lowered by altering the diet to decrease the intake of potassium, promoting intracellular shifts in potassium with insulin, dextrose solutions, and/or beta agonists, and/or exchanging potassium across the gut lumen using potassium-binding resins. Severe acidosis may be corrected with bicarbonate administration. Hematologic abnormalities (such as anemia, uremic platelet dysfunction) may be corrected by transfusion, or administration of desmopressin or estrogens. Further, as the kidneys are especially vulnerable to the toxic effects of various chemicals in patients with AKI, nephrotoxins such as radio-contrast agents, antibiotics with nephrotoxic potential, heavy metal preparations, cancer chemotherapeutic agents and nonsteroidal anti-inflammatory drugs [NSAIDs]) are to be avoided or used with extreme caution. Vasopressor agents should also be carefully selected to avoid undesirable effects. Similarly, medications cleared by renal excretion should be avoided, or their doses should be adjusted appropriately.

A kit useful to determine risk of AKI in a mammal in accordance with the methods described herein is provided in another aspect of the invention. The kit comprises a biomarker-specific reactant for each of IL-6, IL-10 and hFABP (e.g. antibodies specific to each). Each of the reactants is associated with an indicator (e.g. an enzyme, such as horseradish peroxidase (HRP), alkaline phosphatase (AP), β-galactosidase, acetylcholinesterase and catalase) which is capable of yielding a detectable product that is indicative of the concentration of the biomarker in the biological sample, for example, by reacting with a substrate to produce a detectable product. The kit may additionally include instructions for conducting the method and/or indicating that levels of IL-6, IL-6:IL-10 ratio and hFABP that are equal to or exceed a corresponding reference value is indicative of an increase in risk of developing AKI.

Embodiments of the invention are described by reference to the following specific example which is not to be construed as limiting.

Example 1—Determination of Risk of AKI in Children Using h-FABP

Materials and Methods

A multicentre, prospective cohort of children <18 years of age (Participants included children aged 1 month to 18 years) undergoing cardiac surgery (including congenital heart surgery-1 (RACHS-1) category ≥2 surgeries) were used to examine the association of hFABP with the development of post-operative AKI. Children were recruited preoperatively and followed postoperatively until discharge (N=594).

Venous blood samples were collected preoperatively (within 2 months of surgery), on day 1 within 6 hours after surgery, and on postoperative days 2 and 3. Blood was collected in EDTA tubes and centrifuged to separate plasma, divided into bar-coded 0.5-ml cryovials, and stored at −80° C. One preoperative sample vial from each time-point was used for biomarker measurements with a single freeze-thaw. The Evidence Investigator Cytokine Custom Array (Randox) was used to measure h-FABP (ug/L) (CV=17% at 3.4 ug/L and 25 ug/L). Individuals performing measurements were blind to clinical data. Preoperative serum creatinine (sCr) was measured as part of routine clinical care in hospital laboratories using modified Jaffe or enzymatic assays. Finally, preoperative glomerular filtration rates (eGFR) was estimated, expressed as percentiles for age, using the Schwartz equation.

The primary outcome in this study was development of AKI, which was defined as rise in sCr of ≥50% or 0.3 mg/dl from preoperative baseline within the first 7 days after surgery. Severe AKI was defined as either a doubling of creatinine or requirement for dialysis, which has been used in previous pediatric studies. Secondary outcomes included in-hospital mortality, length of in-hospital and intensive care unit (ICU) stays, and time to extubation.

Sample characteristics were compared between patients who developed severe AKI, mild AKI, and no AKI using analysis of variance or Kruskal-Wallis tests for continuous variables and chi-square or Fisher's exact test for categorical variables. Median biomarker values were plotted and compared across AKI groups using Kruskal-Wallis tests. Association between hFABP level and the development of AKI was measured using logistic regression. Biomarker level was introduced into the models as log transformations in order to normalize the distributions of these values. Analyses were repeated adjusting for demographic and preoperative characteristics, including patient age, preoperative eGFR percentile, hospital site, and cardiopulmonary bypass time>120 minutes. Covariates for the models were selected using a combination of previously reported AKI predictors and significance testing using a p-value of 0.1 to determine inclusion. The area under the receiver operating characteristic (ROC) curve (AUC) was calculated to determine the ability to discriminate between patients who did and did not develop AKI. Contingency tables were used to determine the optimal discriminatory cut-point for hFABP.

Continuous net reclassification improvement (NRI) and integrated discrimination improvement (IDI) indices were also calculated. The NRI indicates how much more frequently appropriate reclassification of AKI risk occurs than inappropriate reclassification with use of the model containing the biomarker. Similarly, the IDI can be thought of as a measure of how far individuals are moving on average along the continuum of predictive risk. In general, these measures of biomarker assessment directly quantify the appropriateness and amount of overall reclassification when biomarker values are added to the clinical prediction models.

To determine whether hFABP also predicted longer ICU and hospital stays, the association between these biomarkers and ICU and hospital length-of-stays using logistic regression was evaluated. ICU and hospital stays were dichotomized using the median value of each (3 days for ICU stay and 7 days for hospital stay). Models were adjusted for patient and clinical characteristics as well as AKI status to determine whether AKI explained the longer lengths of stay in patients with high cardiac biomarker values. Finally, as a sensitivity analysis, all analyses described above were repeated with severe AKI as the outcome in order to determine whether hFABP performed comparably when a more severe outcome was modeled.

Results

Of the 106 pediatric patients enrolled in this study, 55 (52%) developed AKI after cardiac surgery. Patients who developed AKI had higher median levels of pre- and post-operative hFABP compared with patients without AKI (p<0.01).

Figure 2:
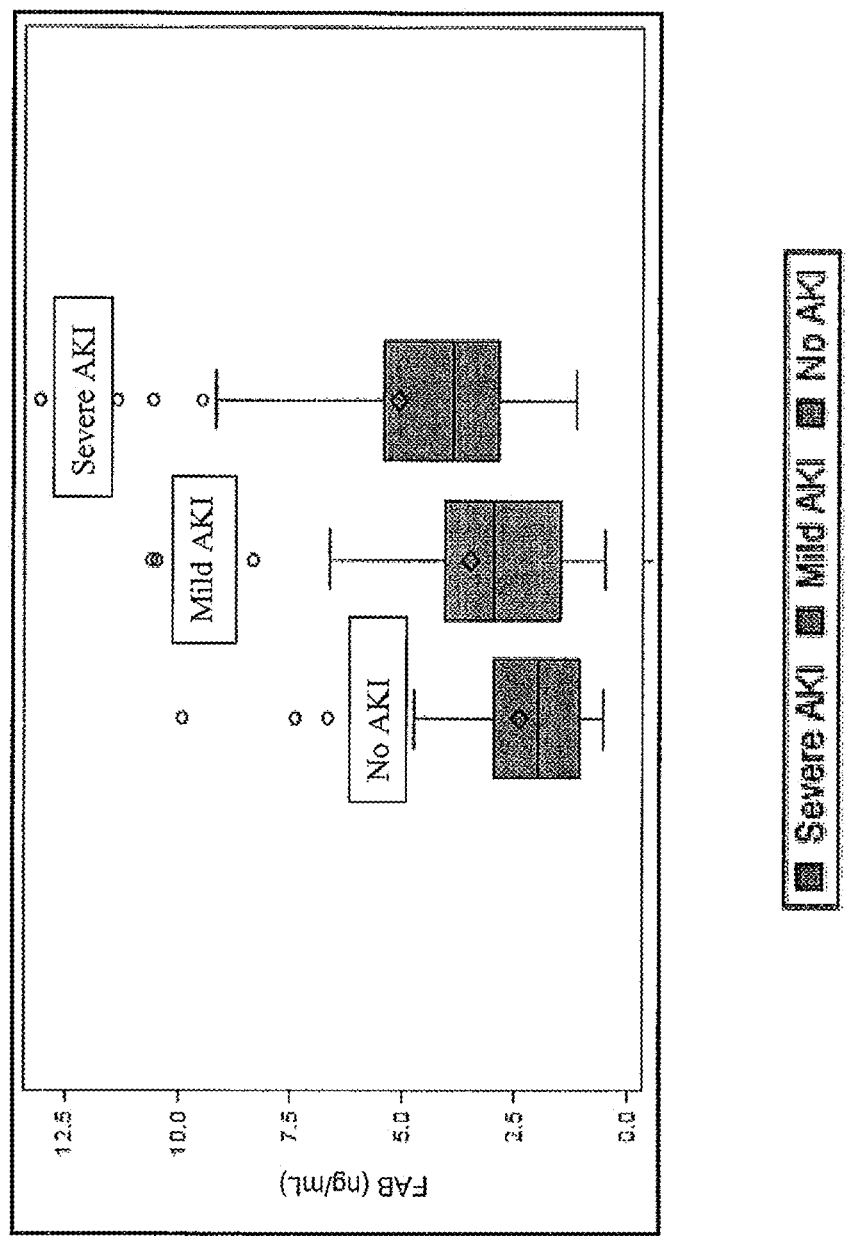
FIG. 2 illustrates the distribution of plasma values of preoperative cardiac biomarkers by AKI status.

The trajectory of h-FABP median level during the first three days of hospitalization stratified by AKI status is displayed in FIG. 1. h-FABP median level peaked within 6 hours after surgery. Across all four time-points, median h-FABP levels tended to be higher among patients who developed severe AKI compared with patients with mild or no AKI. FIG. 2 shows the distribution of hFABP stratified by AKI status. Preoperative levels of h-FABP were associated with higher odds of developing AKI in unadjusted analysis. After adjustment for patient characteristics, the association of preoperative h-FABP with development of postoperative AKI remained significant. Thus, pre-operatively, higher levels of hFABP were associated with increased odds of developing AKI (hFABP adjusted odds ratio 2.76, 95% CI 1.27-6.03) (FIG. 5).

Figure 3:
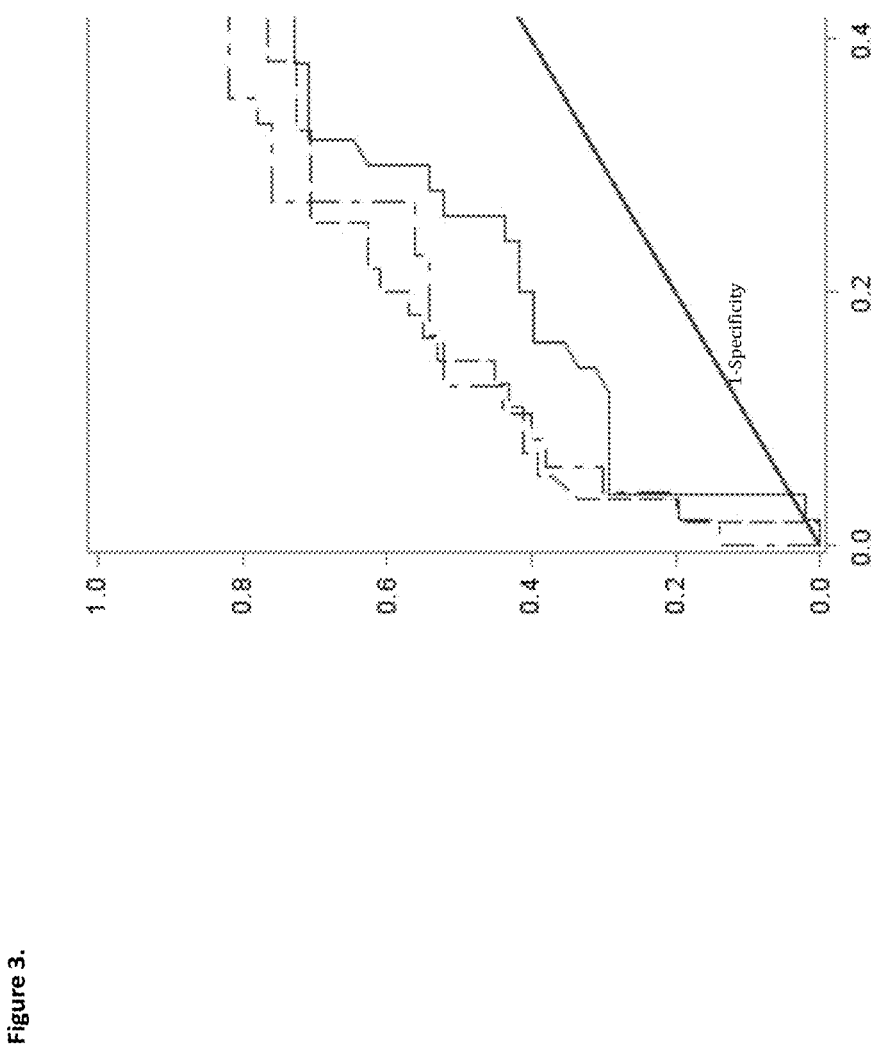
FIG. 3 shows receiver operating curves for biomarkers alone and combined with clinical model. Preoperative FABP—models containing biomarkers alone are represented by solid blue lines, clinical models are represented by dotted red lines, and models containing both biomarker and clinical variables are represented by punctuated green lines.

A one-unit increase in log h-FABP was associated with a 2.8-fold increase in the odds of developing postoperative AKI. ROC analyses revealed preoperative h-FABP to be a candidate marker with high discriminatory value for predicting AKI (FIG. 3). When used alone, preoperative h-FABP had a relatively high AUC (AUC 0.70 (95% CI: 0.60-0.81)). Adding preoperative h-FABP to the clinical model did not significantly improve the AUC of the clinical model (p=0.57) (FIG. 6); however, hFABP was associated with significant NRI and IDI values (FIG. 7). The optimal cut-off for detecting postoperative AKI was 2.6 pg/mL (sensitivity 68.%, specificity 68.8%) for preoperative h-FABP.

A summary of different clinical characteristics of preoperative hFABP concentrations is provided in Table 1:

TABLE 1

Cut-off values for predicting acute kidney injury

| Biomarker Value | Sensitivity | Specificity | PPV | NPV |
|---|---|---|---|---|
| Preoperative FABP (ug/L) | | | | |
| 90% Sensitivity 1.3 | 90.0 | 29.2 | 57.0 | 73.7 |
| Optimal 2.6 | 68.0 | 68.8 | 69.4 | 67.4 |
| 90% Specificity 4.8 | 26.0 | 91.7 | 76.5 | 54.3 |

Abbreviations:
NPV, negative predictive value;
PPV, positive predictive value.

Figure 4:
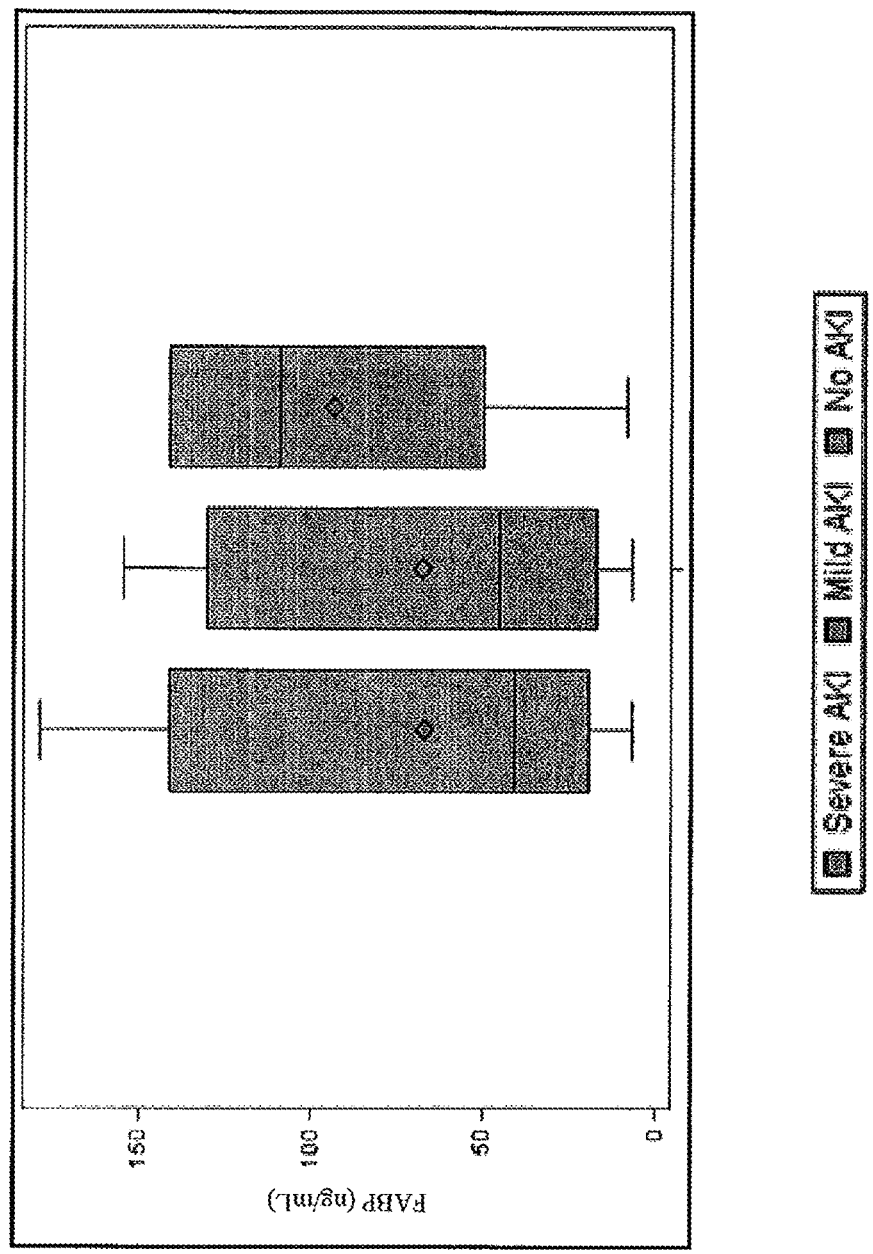
FIG. 4 shows the distribution of plasma values of postoperative day 1 cardiac biomarkers by AKI status.

Distribution of hFABP on postoperative day 1 is presented in FIG. 4. Median levels of hFABP differed significantly across AKI groups.

To determine whether hFABP could also be used to predict more severe forms of AKI, the analyses above was repeated for severe AKI. Results were similar for AKI and severe AKI. Higher levels of preoperative h-FABP were associated with increased odds of developing postoperative severe AKI. NRI/IDI analyses indicated that this marker improves prediction of severe AKI when added to the clinical models. In postoperative analyses, h-FABP was associated with increased odds of postoperative severe AKI.

When combined with other clinical variables (pre-operative clinical models adjusted for age (years), site, and pre-operative eGFR percentile), pre-operative hFABP provided good discrimination producing an area under the curve (AUC) of 0.78, as compared to the clinical model alone at 0.74 (FIG. 6).

Thus, an increase in pre-operative and post-operative hFABP is associated with an increase length of stay in the intensive care unit and an increased risk of post-operative AKI and provides good discrimination of patients who develop AKI. Such pre-operative and post-operative biomarkers are useful for risk stratification of paediatric patients undergoing cardiac surgery.

Example 2—Determination of Risk of AKI in Children Using IL-6 and IL-10

Children undergoing cardiac surgery may exhibit a pronounced inflammatory response to cardiopulmonary bypass (CPB). The aim of this study was to evaluate the association of two inflammatory cytokines, interleukin IL-6 and IL-10, with AKI and other adverse outcomes in children after cardiac surgery.

This is a sub-study of the study described in Example 1 (TRIBE-AKI cohort), including 106 children from 1 month to 18 years old, undergoing CPB. Plasma IL-6 and IL-10 were measured preoperatively (within 2 months prior to surgery) and postoperatively on day 1 (within 6 hours after surgery). IL-6 and IL-10 samples were analyzed on the Randox Evidence Investigator™ using a Randox developed custom cytokine array (Randox Laboratories Ltd). The detection range for IL-6 is 0.6-790 pg/ml, and for IL-10 is 0.9-840 pg/ml.

The primary outcome was the development of severe AKI, defined by receipt of acute dialysis during the entire hospital stay or a doubling in serum creatinine from the baseline preoperative value (consistent with Risk Injury Failure Loss End-Stage Kidney Disease[RIFLE] stage I or the Acute Kidney Injury Network (AKIN) stage 2 AKI). Pre- and postoperative serum creatinine levels were measured in the same clinical laboratory for each patient at all sites. Secondary outcomes included mild AKI (defined by a ≥50% rise of baseline serum creatinine), in-hospital mortality, length of in-hospital and intensive care unit (ICU) stay, and time to extubation.

Continuous variables were compared with two-sample t test or Wilcoxon rank sum test and dichotomous variables with the chi-squared test or Fisher's exact test. For calculation of p-values, ANOVA was used for each mean comparison and Kruskal-Wallis tests were used for median comparisons. To evaluate the association of each biomarker with AKI, the cohort was divided into tertiles on the basis of blood IL-6 or IL-10 levels. Mixed logistic regression models with random intercepts for each center were used to determine the adjusted odds ratios of AKI. Adjustments were made for important covariates that predict AKI in the pediatric cardiac surgery setting including age, gender, race, and surgical site. Poisson regression with log link function was used to estimate the association between biomarkers and clinical outcomes: number of days to extubation, length of intensive care unit stay and length of hospital stay. Biomarker values below the assay's detectable limit were assigned the lower limit of detection.

Results

Median preoperative plasma IL-6 levels were found to be significantly different between patients with severe AKI vs. without severe AKI (2.6 pg/mL vs. 0.6 pg/mL; p=0.03). There was no significant difference in IL-10 levels, preoperatively (p=0.8).

Severe AKI, defined by dialysis or a doubling of baseline creatinine concentration was diagnosed in 24 patients (23%). Preoperative IL-6 was significantly higher in patients with severe AKI (defined by receipt of acute dialysis during the entire hospital stay or a doubling in creatinine concentration from the baseline preoperative value consistent with Risk Injury Failure Loss End-Stage Kidney Disease[RIFLE] [stage I or the Acute Kidney Injury Network (AKIN) stage 2 AKI)) versus without severe AKI (i.e., Severe AKI median (interquartile range), 2.6 (0.6-4.9) vs. without severe AKI median (interquartile range), 0.6 (0.6-2.2); p=0.03). After adjustment for age, gender, race, and study site, the highest preoperative IL-6 tertile was associated with an eight-fold increased risk for severe AKI compared with the lowest tertile (adjusted OR 7.9 (CI: 1.7-37)).

Plasma levels of IL-6 increased significantly after surgery in those patients with severe AKI (pre-op IL-6 median=2.6, post-op 0-6 hours median=107.3, post-op day 3 median=59.4) peaking on day 1 (0-6 hours), postoperatively. Elevated IL-6 on day 3 was associated with longer hospital stay (p=0.0001).

More specifically, preoperative biomarker measurements were categorized into tertiles of IL-6 and IL-10 (Table 2). The third tertile of IL-6 was significantly associated with an eight-fold odds of severe AKI after adjusting for clinical and demographic variables. None of the preoperative tertiles of IL-10 were associated with severe AKI.

pg/mL) (p=0.001). Otherwise, IL-10 and IL-6 were not found to be significantly different in the severe AKI or mild AKI, groups post-operatively. Of note, 68% of day 3 IL-10 values were undetectable.

The average lengths of stay in the PICU and in the hospital for the entire cohort were 5.5 days (SD, 7.3) and 10 days (SD, 9.9), respectively. The average length of mechanical ventilation for the entire cohort was 2.3 days (SD, 1.6). Postoperatively, on day 3, plasma IL-6 was linearly associated with a longer length of hospital stay. Early postoperative levels of IL-6 or IL-10 were not associated with length of ICU stay or length of mechanical ventilation.

Thus, children undergoing cardiac surgery at highest risk for development of post-op AKI exhibit increased preoperative hFABP plasma levels and increased IL-6 plasma levels (or IL-6:IL-10 ratio). (see Table 3 below).

TABLE 2

Logistic regression models for development of Severe Acute Kidney Injury

| Biomarker Tertile | Range (pg/mL) | Unadjusted OR (95% CI) | p-value | Adjusted* OR (95% CI) | p-value |
|---|---|---|---|---|---|
| IL-6 pre-op | | | | | |
| T1, n = 41 | (0.6-0.6) | 1.0 (referent) | 0.03 | 1.0 (referent) | 0.02 |
| T2, n = 14 | (1.4-2.2) | 1.5 (0.3, 9.5) | | 1.2 (0.1, 11) | |
| T3, n = 27 | (2.2-76.8) | 5.4 (1.5, 20) | | 7.9 (1.7, 37) | |
| IL-6 day 1 | | | | | |
| T1, n = 35 | (17.9-63.4) | 1.0 (referent) | 0.7 | 1.0 (referent) | 0.4 |
| T2, n = 35 | (63.4-126.7) | 1.4 (0.4, 4.7) | | 1.7 (0.5, 6.2) | |
| T3, n = 35 | (135-313.7) | 1.7 (0.5, 5.3) | | 2.5 (0.7, 8.9) | |
| IL-6 day 3 | | | | | |
| T1, n = 31 | (0.6-22.5) | 1.0 (referent) | 0.4 | 1.0 (referent) | 0.2 |
| T2, n = 32 | (22.7-63.9) | 0.9 (0.3, 3.4) | | 0.3 (0.1, 1.5) | |
| T3, n = 31 | (65.7-683) | 2.0 (0.6, 6.4) | | 1.0 (0.2, 3.8) | |
| IL-10 pre-op† | | | | | |
| T1, n = 63 | (0.9-0.9) | 1.0 (referent) | 0.7 | 1.0 (referent) | 0.4 |
| T2, n = 18 | (1.3-21.6) | 1.2 (0.4, 4.4) | | 0.4 (0.1, 3.0) | |
| IL-10 day 1 | | | | | |
| T1, n = 34 | (3.1-70.3) | 1.0 (referent) | 0.1 | 1.0 (referent) | 0.05 |
| T2, n = 35 | (71.2-110.2) | 3.9 (1.1, 14) | | 4.1 (1.1, 16.1) | |
| T3, n = 35 | (112.8-545.2) | 1.9 (0.5, 7.1) | | 1.2 (0.3, 5.2) | |
| IL-10 day 3‡ | | | | | |
| T1, n = 52 | (0.9-0.9) | 1.0 (referent) | 0.02 | 1.0 (referent) | 0.1 |
| T2, n = 25 | (1.4-59.2) | 3.8 (1.3, 11) | | 3.1 (0.9, 10) | |

*Adjusted for age, gender, race, surgical site;
†IL-10 pre-op were undetectable in 78% of the sample and are in T1;
‡IL-10 day 3 were undetectable in 68% of the sample and are in T1.

Figure 8:
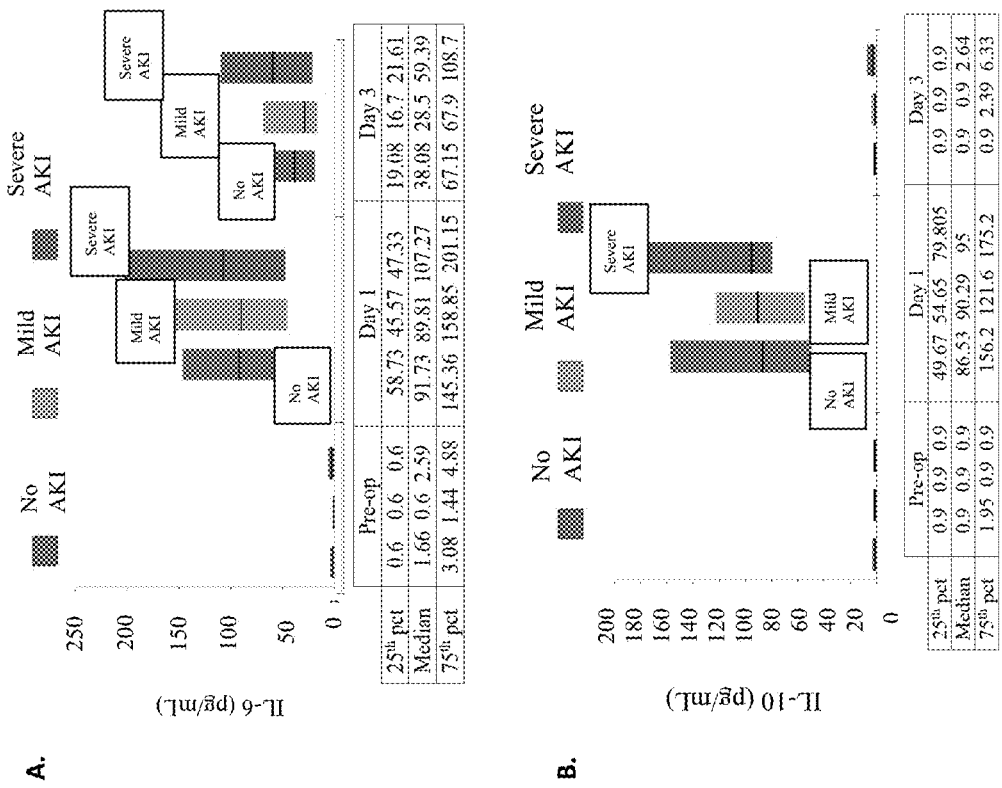
FIG. 8 shows biomarker distribution by AKI status. A) IL-6 and B) IL-10.
Figure 9:
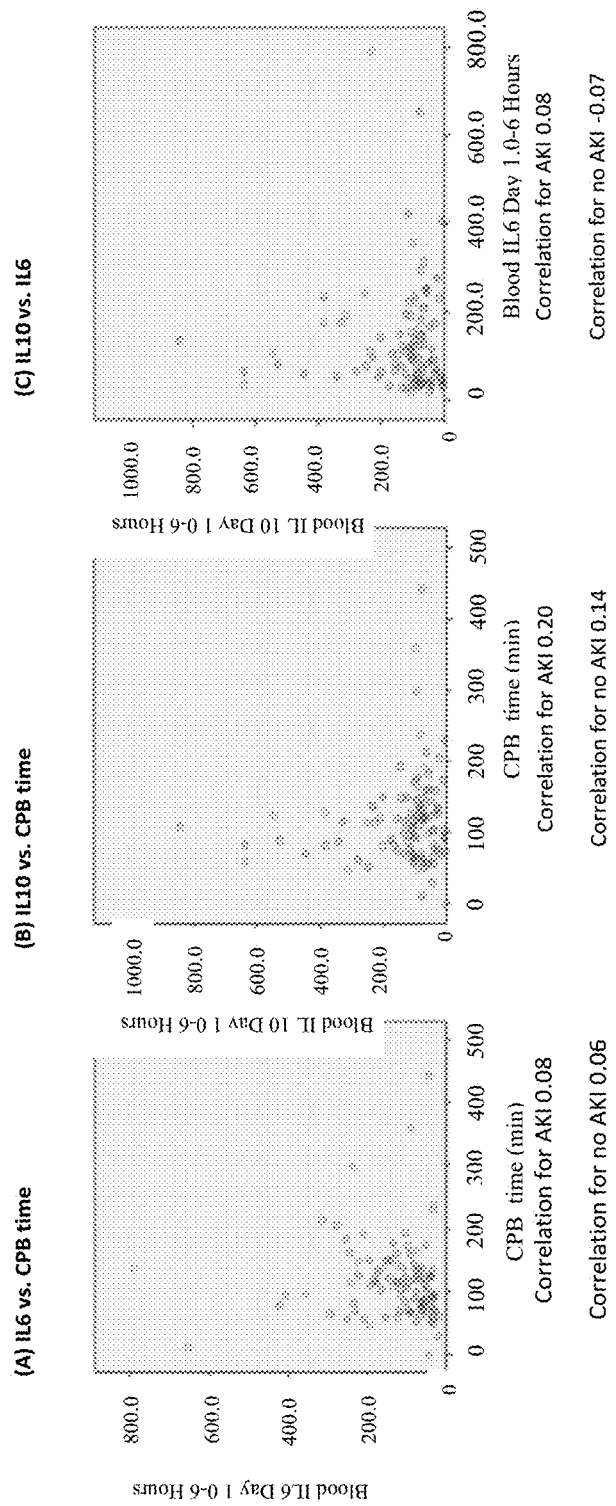
FIG. 9 illustrates scatterplots of postoperative biomarkers, A) IL-6 vs. CPB time, B) h-FABP vs. CPB time and C) IL-6 vs. IL-10.

Plasma IL-6 and IL-10 concentrations, collected within 6 hours of arrival in the pediatric ICU (PICU), peaked at this first postoperative collection and then declined on day 3 (FIG. 8). The decline was more abrupt for IL-10 from day 1 to day 3, in comparison to IL-6. From day 1 to day 3, mean levels of all patients declined from 135 pg/mL to 3.1 pg/mL in IL-10 and from 128 pg/mL to 70 pg/mL in IL-6. IL-6 remained elevated on day 3, whereas IL-10 had returned to preoperative levels (FIG. 8). AKI was most frequently diagnosed on day 2 after surgery. FIG. 9 demonstrates that IL-6, IL-10, and CPB time were only weakly correlated with each other. On day 1, there was no statistically significant difference between the patients with and without severe AKI in plasma IL-6 (p=0.4) and IL-10 levels (p=0.3).

On day 3, there was a statistically significant difference in median plasma IL-10 levels in the patients with severe AKI (2.6 pg/mL) versus the patients without severe AKI (0.9

TABLE 3

Biomarker concentrations in children by severe AKI status

| Biomarkers | Time point | Severe AKI (n = 24) | No Severe AKI (n = 82) | P-value* |
|---|---|---|---|---|
| hFABP | Pre-op | 3.88 (2.84, 5.42) | 2.13 (1.29, 3.47) | <0.001 |
| | Post-op | 108.9 (49.9, 141) | 42.8 (17.9, 141) | 0.044 |
| IL-6 | Pre-op | 3.10 (1.19, 5.36) | 0.60 (0.60, 2.18) | 0.012 |
| | Post-op | 108.8 (51.0, 209.2) | 89.8 (51.9, 149.6) | 0.305 |

TABLE 3-continued

Biomarker concentrations in children by severe AKI status

| Biomarkers | Time point | Severe AKI (n = 24) | No Severe AKI (n = 82) | P-value* |
|---|---|---|---|---|
| IL-6:IL-10 | Pre-op | 2.47 (0.67, 5.42) | 0.67 (0.67, 2.16) | 0.199 |
|  | Post-op | 1.00 (0.62, 2.41) | 1.00 (0.48, 2.75) | 0.925 |

Median (IQR) reported.
Severe AKI is defined as receipt of dialysis or doubling of creatinine concentration.
*p- values from Wilcoxon comparing patients with and without severe AKI.

Example 3—Determination of Risk of AKI in Adults Using IL-6 and IL-10

To investigate the utility of IL-6 and IL-10 as biomarkers of AKI and mortality in adults (e.g. greater than 18 yrs of age), an ancillary analysis was conducted of a large, prospective study of adults at risk for AKI who underwent cardiac surgery. Patients undergoing cardiac surgery at high risk for AKI were enrolled at six academic centers. AKI was defined as a doubling in creatinine concentration from baseline or receiving acute dialysis during the hospital stay. IL-6, IL-10, and the IL-6:IL-10 ratio were evaluated for association with outcomes of AKI or all-cause mortality at a mean follow-up of 3 years.

Generally, elevated pre-operative IL-6:IL-10 ratio was independently associated with risk of AKI (adjusted odds ratio [OR] 3.2, 95% confidence interval [CI]: 1.1-9.6) and death (adjusted hazards ratio [HR]=1.4, 95% CI:1.1-2.0). Elevated first postoperative IL-6 was associated with increased risk of AKI (OR=6.4, 95% CI: 2.2-18.7), though the association was attenuated following adjustment (OR=3.0, 95% CI: 0.94-9.5). At all postoperative time points, IL-10 was protective with higher levels independently associated with lower risk of mortality (day 1 adjusted HR=0.71, 95% CI: 0.56-0.92). There was significant interaction by plasma neutrophil gelatinase-associated lipocalin (NGAL), an established AKI biomarker, on the association of IL-10 and mortality, such that the independent protective effect conferred by IL-10 was only observed in patients with NGAL levels above the median (P=0.01). Thus, plasma levels of IL-6 and IL-10 are independently associated with both short- and long-term kidney injury-related outcomes after cardiac surgery.

Figure 12:
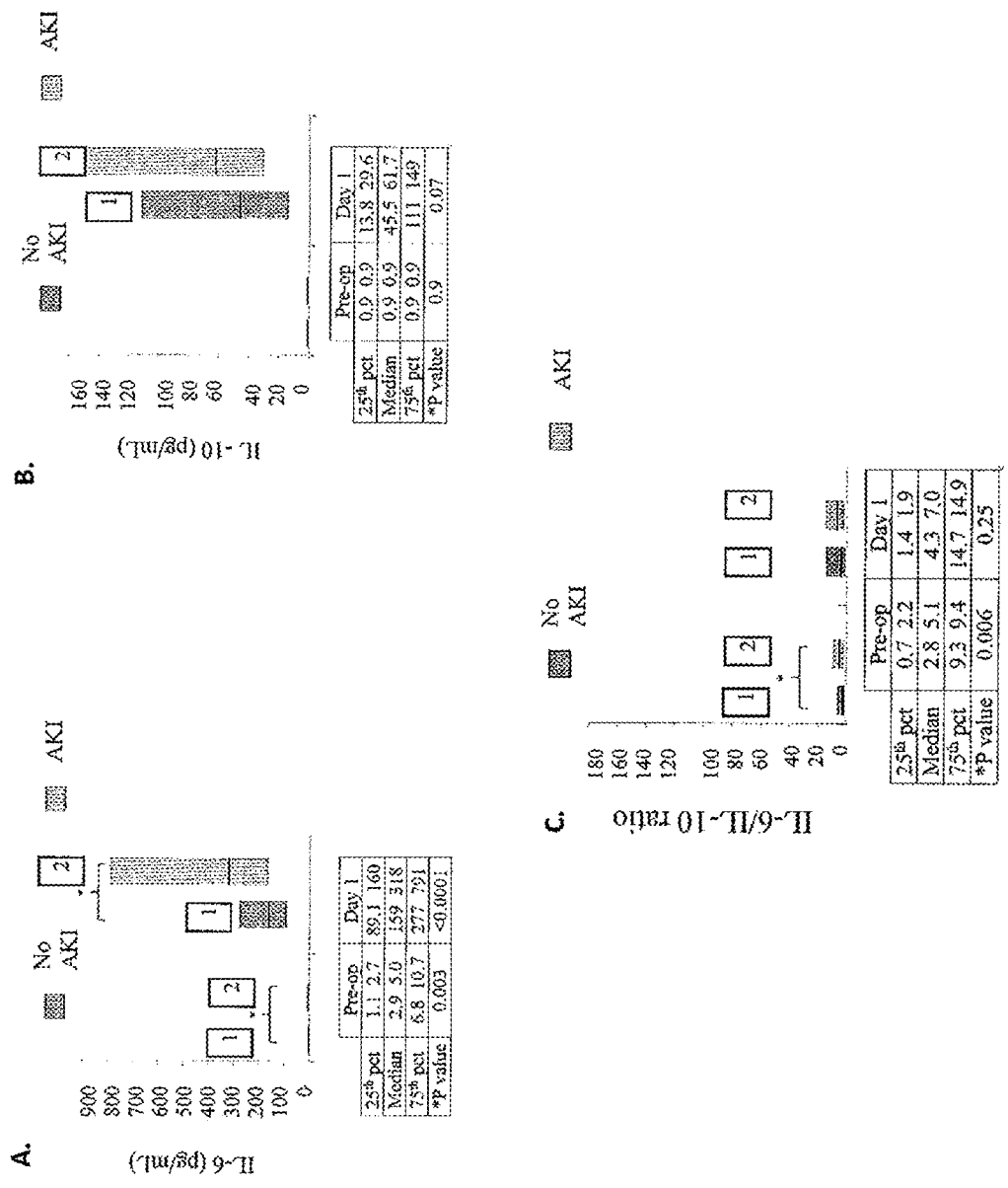
FIG. 12 shows: A) IL-6 levels by AKI status; B) IL-10 levels by AKI status; C) IL-6:IL-10 ratio levels by AKI status. Each bar represents the interquartile range ($25^{th}$ percentile to $75^{th}$ percentile) and the horizontal black line represents the median; *=p<0.05.

More specifically, preoperative IL-6 levels were significantly higher in those who developed AKI compared to those who did not (median of 5.0 pg/ml versus 2.9 pg/ml, P=0.003) (FIG. 12a). While levels of IL-6 were elevated in both AKI and non-AKI groups at all postoperative time points, including the first postoperative (0-6 hours), day 2, and day 3, IL-6 levels were higher at each of these three time points in those who developed AKI compared to those who did not (medians of 318 pg/ml versus 159 pg/ml, P<0.0001; 189 pg/ml versus 153 pg/ml, P=0.003; 179 pg/ml versus 118 pg/ml, P<0.001, respectively). IL-6 levels peaked between 0-6 hours after surgery.

Preoperative IL-10 levels were not significantly different between patients who did and did not develop AKI (FIG. 12b). Levels of IL-10 were also increased at each of the three postoperative time points in both AKI and non-AKI groups. Median IL-10 levels peaked within 6 hours in a seemingly parallel manner to IL-6, though at lower absolute values and seemed to decline more abruptly.

The preoperative IL-6:IL-10 ratio significantly differed between those who did and did not develop AKI (median ratio of 5.1 versus 2.8, p=0.006) (FIG. 12c).

The unadjusted and adjusted associations of preoperative IL-6, IL-10, and the IL-6:IL-10 ratio with AKI are shown in Table 4. Only the preoperative IL-6:IL-10 ratio was independently associated with the outcome of postoperative AKI. The highest tertile (>ratio) was associated with an over three-fold increased risk for AKI compared to the lowest tertile (adjusted odds ratio [OR]=3.2, 95% CI: 1.1-9.6).

TABLE 4

Tertiles of preoperative inflammatory biomarkers and risk of AKI

| Biomarker | AKI n (%) | Odds ratio (95% CI) Unadjusted | Adjusted |
|---|---|---|---|
| IL-6 (pg/mL) | | | |
| T1 (0.6-1.9) | 8 (2.6%) | 1.00 (referent) | 1.00 (referent) |
| T2 (2.0-5.2) | 8 (2.6%) | 1.01 (0.37, 2.72) | 1.09 (0.39, 3.08) |
| T3 (5.2-633) | 17 (5.5%) | 2.20 (0.93, 5.17) | 2.17 (0.84, 5.63) |
| IL-10 (pg/mL) | | | |
| T1 (0.9) | 28 (3.4%) | 1.00 (referent) | 1.00 (referent) |
| T2 (1.5-168) | 3 (3.2%) | 0.93 (0.28, 3.10) | 0.96 (0.26, 3.61) |
| IL-6:IL-10 ratio | | | |
| T1 (0.03, 1.7) | 5 (1.7%) | 1.00 (referent) | 1.00 (referent) |
| T2 (1.7, 4.7) | 10 (3.3%) | 2.03 (0.69, 6.00) | 2.35 (0.76, 7.24) |
| T3 (4.7, 386) | 16 (5.3%) | 3.31 (1.20, 9.16) | 3.19 (1.06, 9.56) |

Adjusted for age, sex, white race, non-elective surgery, pre-op eGFR, diabetes, hypertension, centre, congestive heart failure, myocardial infarction, pre-op urine albumin to creatinine ratio, and type of surgery; OR = odds ratio, CI = confidence interval.
Number of patients per Tertile: IL-6 T1 n = 309, T2 n = 307 T3 n = 308; IL-10 T1 n = 814, T2 n = 94; IL-6/IL-10 ratio T1 n = 302, T2 n = 303, T3 n = 303.

First postoperative biomarker values and the associated risks of AKI are presented in Table 5. While the highest tertile of first postoperative IL-6 was associated with a higher risk of AKI compared to the lowest tertile (unadjusted OR=6.4, 95% CI: 2.2-18.7), the association was attenuated following multivariable-adjustment (adjusted OR=3.0, 95% CI: 0.94-9.5).

TABLE 5

Tertiles of first postoperative inflammatory biomarkers and risk of AKI

| Biomarker | AKI n (%) | Odds Ratio (95% CI) Unadjusted | Odds Ratio (95% CI) *Adjusted |
|---|---|---|---|
| IL-6 (pg/mL) | | | |
| T1 (6.2-111) | 4 (1.3%) | 1.00 (referent) | 1.00 (referent) |
| T2 (111-239) | 9 (2.8%) | 2.28 (0.70, 7.48) | 1.51 (0.44, 5.26) |
| T3 (241-791) | 24 (7.5%) | 6.41 (2.2, 18.69) | 2.99 (0.94, 9.51) |
| IL-10 (pg/mL) | | | |
| T1 (0.9-21.7) | 8 (2.5%) | 1.00 (referent) | 1.00 (referent) |
| T2 (21.8-79.5) | 16 (5%) | 2.05 (0.86, 4.85) | 1.47 (0.53, 4.07) |
| T3 (79.6-841) | 13 (4.1%) | 1.65 (0.68, 4.04) | 1.03 (0.33, 3.18) |
| IL-6/IL-10 ratio | | | |
| T1 (0.07, 2.2) | 12 (3.8%) | 1.00 (referent) | 1.00 (referent) |
| T2 (2.2, 8.9) | 10 (3.1%) | 0.83 (0.35, 1.94) | 0.75 (0.31, 1.85) |
| T3 (8.9, 878) | 15 (4.7%) | 1.26 (0.58, 2.74) | 1.31 (0.53, 3.25) |

*Adjusted for age, sex, white race, CPB time >120 minutes, non-elective surgery, pre-op eGFR, diabetes, hypertension, centre, congestive heart failure, myocardial infarction, pre-op urine albumin to creatinine ratio, and type of surgery; OR = odds ratio, CI = confidence interval.

Figure 13:
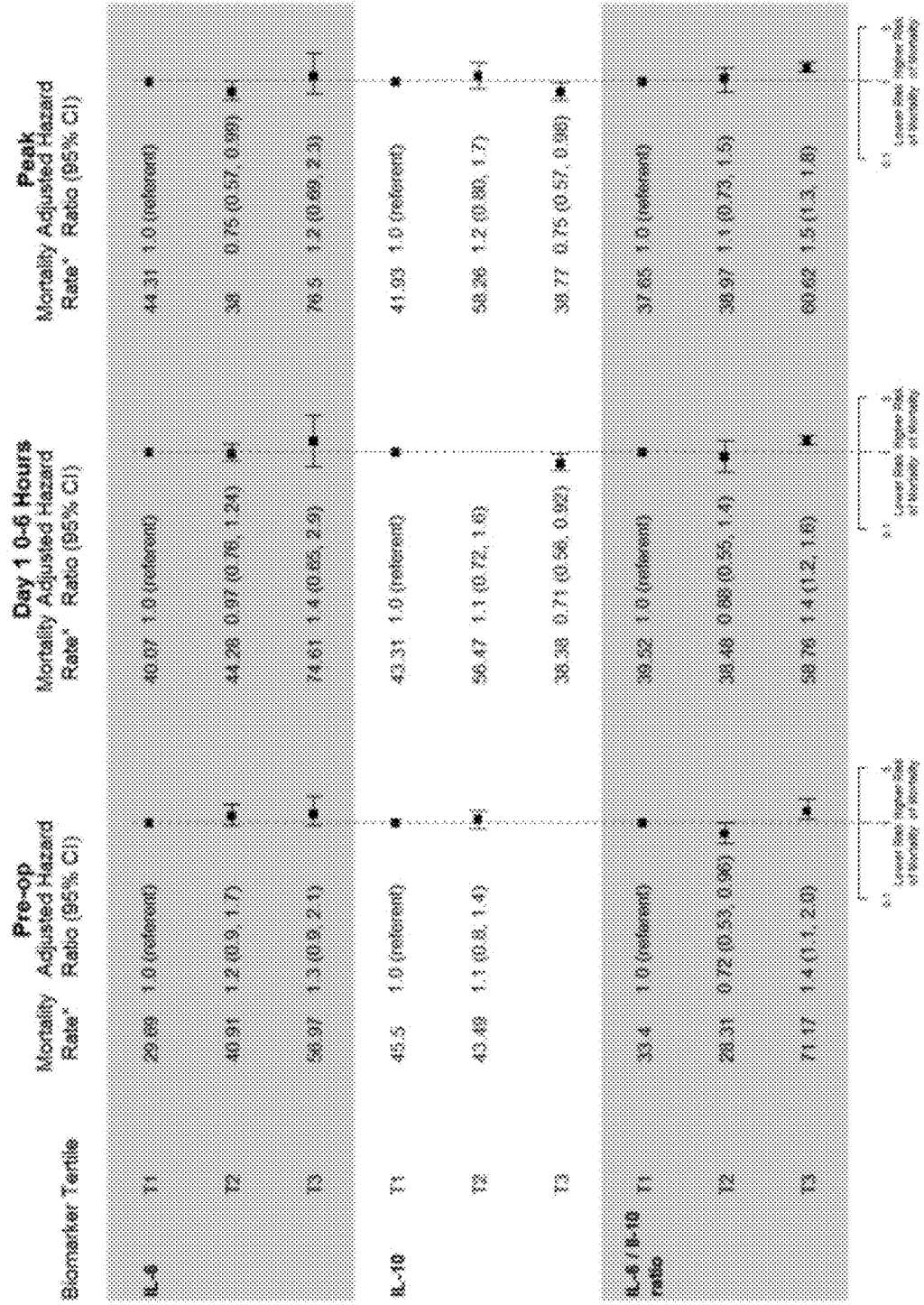
FIG. 13 shows the association of Pre and Postoperative Biomarker Levels with Mortality. *Mortality rate per 1000 patient years adjusted for site. Adjusted for age (per year), sex, white race, CPB time>120 minutes, non-elective surgery, pre-op eGFR, diabetes, hypertension, site, congestive heart failure, myocardial infarction, pre-op UACR, and type of surgery. Models with pre-op biomarkers were not adjusted for CPB time>120 minutes.

Increased IL-6:IL-10 ratio was independently associated with a higher risk of all-cause mortality both pre- and post-surgery (FIG. 13). In multivariable-adjusted analyses, the highest tertile of preoperative IL-6:IL-10 ratio was significantly associated with higher risk for all-cause mortality (hazard ratio [HR]=1.4, 95% CI:1.1-2.0). The third tertile of the IL-6:IL-10 ratio measured postoperatively both at the first postoperative time point and peak levels were independently associated with increased risk of all-cause mortality following multivariable-adjusted analyses (adjusted HR=1.4, 95% CI: 1.2-1.6; adjusted HR=1.5, 95% CI: 1.3-1.8, respectively). Elevated levels of IL-10 measured postoperatively both at the first postoperative time and peak levels were significantly associated with lower risk of all-cause mortality following multivariable-adjusted analyses (adjusted HR=0.71, 95% CI: 0.56-0.92; HR=0.75, 95% CI: 0.57-0.98, respectively; FIG. 13).

Example 4—Determination of Risk of AKI in Adults Using hFABP

A study to evaluate whether blood levels of hFABP in adults predict development of AKI and help to distinguish a subgroup of AKI due to cardiac dysfunction versus true tubular damage.

The Translational Research Investigating Biomarker Endpoints in Acute Kidney Injury (TRIBE-AKI) cohort was a prospective cohort of 1219 adult patients who underwent cardiac surgery at six academic institutions across North America and who were at high risk for post-operative AKI. The primary outcome was severe post-operative AKI, defined as doubling of serum creatinine or requiring dialysis. hFABP analysis was conducted as described in Example 1.

On average, patients who experienced severe AKI had higher levels of hFABP, both pre-operatively and post-operatively, than patients who did not experience AKI (Table 6).

TABLE 6

Biomarker concentrations by AKI status

| Biomarker | Time point | AKI (n = 37) | No AKI (n = 918) | p-value* |
|---|---|---|---|---|
| hFABP | Pre-op | 6.3 (3.2-7.8) | 4.0 (2.8-5.7) | 0.0123 |
|  | Post-op | 77.4 (38.5-141.0) | 30.3 (20.8-47.1) | <0.0001 |
| IL-6 | Pre-op | 5.6 (2.7-8.3) | 2.9 (1.2-7.1) | 0.0368 |
|  | Post-op | 343.2 (173.5-791.0) | 161.0 (89.4-283.0) | <0.0001 |
| IL-6:IL-10 ratio | Pre-op | 4.7 (1.9-8.9) | 2.8 (0.7-6.2) | 0.0447 |
|  | Post-op | 7.0 (1.9-14.9) | 4.3 (1.4-14.7) | 0.3106 |

Median (IQR) reported.
*P-value from Wilcoxon comparing biomarker concentrations in patients with and without AKI In analyses that adjusted for known AKI risk factors, hFABP levels within the first 6 hours post-operatively remained an independent predictor for incidence of AKI (adjusted OR 5.4 [2.9, 10.1]). Notably, this relationship persisted even after adjustment for change in creatinine concentration (adjusted OR 3.7 (1.9-7.4). In addition, when adjusted for urine interleukin-18 levels (IL-18) levels, which represent the damage to the renal tubular cells, hFABP was still independently associated with severe AKI (adjusted OR 2.9 [1.4, 5.8]).

Thus, elevated blood hFABP level within the first six hours post-operatively is an independent predictor for developing severe AKI in adults. hFABP levels identify a subset of patients with severe AKI that did not sustain severe tubular injury.

Increased plasma levels of peri-operative (pre and first post-op) hFABP and IL-6:IL-10 ratio identifies patients at highest risk for post-operative AKI (see Table 7).

TABLE 7

Biomarker combinations of IL-6 and hFABP

| Time point | Unadjusted OR (95% CI) | Model 1 OR (95% CI) | Model 2 OR (95% CI) | AUC from ROC Curve |
|---|---|---|---|---|
| Pre-op | IL-6-1.11 (0.84, 1.48) hFABP-1.88(1.01, 3.52) | IL-6-1.24 (0.90, 1.70) hFABP-1.78 (0.76, 4.18) | NA | 0.63 |
| Post-op | IL-6-2.01 (1.29, 3.15) hFABP-4.07(2.41, 6.85) | IL-6-1.68 (1.01, 2.77) hFABP-4.90 (2.70, 8.88) | IL-6-1.75 (0.98, 3.13) hFABP-3.64(1.83, 7.22) | 0.80 |

Model 1: Adjusted for Age (per year), sex, white race, non-elective surgery, diabetes, hypertension, centre, Congestive heart failure (chf), Myocardial Infarction (mi), Pre-op urine albumin to creatinine ratio, and Type of surgery (cabg or valve vs. all others). Post-op biomarkers are also adjusted for CPB time >120 minutes
Model 2: Model 1 + change in serum creatinine day 10-hours from-pre-op Linear combinations of two diagnostic test results can be analysed with the purpose of obtaining a maximal AUC for the combined score (Pepe, M. S. & Thompson, M. L., 2000, Biostatistics 1: 123-40).

Statistical analysis for this clinical study was performed using SPSS 16.0 (SPSS Inc, Chicago, Ill.) and MedCalc 11.5 (Mariakerke, Belgium). Categorical data were reported as percentages with 95% confidence interval of the mean percentage, and compared using Fisher's exact test. After testing for normal distribution, continuous data were reported as median with 25th-75$^{th}$ percentiles and non-parametric data was compared using the Mann-Whitney U test; continuous data over time were compared using the one-way repeated measures analysis of variance by ranks (Friedman test). We used nonparametric bivariate correlation and reported Spearman correlation coefficients (r). The ability of biomarkers to predict AKI was assessed by plotting receiver-operator characteristic (ROC) curves and further reported as areas under the curves (AUC) with 95% confidence intervals. An AUC-ROC value of >0.7 was taken to indicate a reasonable and >0.8 a good biomarker performance. AUC-ROC differences>0.1 units were defined as significant. ROC curve optimal cut-off values for AKI diagnosis, for curves with a statistically significant AUC, were defined as the point that maximized the Youden index, defined as (sensitivity+specificity)−1 (Youden W J, Cancer 1950, 3:32-35).

Univariate and multivariate stepwise regression analysis was undertaken to assess predictors of no AKI after CPB. Variables tested on univariate relation with incidence of no AKI included clinically relevant variables all displayed in the Figure legends, type and duration of surgery and renal biomarkers at 6 hours after start of CPB. Multivariate logistic regression modelling included clinically relevant variables with univariate P value<0.1 (age, atrial fibrillation, left ventricular ejection fraction [LVEF]<35%, chronic obstructive pulmonary disease [COPD], peripheral vascular disease [PVD]) and renal biomarkers. Logarithmic transformations were applied when necessary before multivariable logistic regression analyses were performed. Statistical significance was denoted by two sided P values of <0.05.

Example 5—Risk of AKI Using Combination of hFABP, IL-6 and IL-6:IL-10

The different biomarkers as well as combination of biomarkers were assessed in a first postoperative blood sample (i.e. 0-6 h post surgery sample) for predicting AKI in adult samples. Determination of the level of hFABP, hFABP+IL-6 and hFABP+IL-6:IL-10 ratio yielded the highest AUC, sensitivity and specificity as a predictor of AKI risk. High concentrations of hFABP (>upper limit of normal)+IL-6:IL-10 ratio yielded a somewhat higher specificity as compared to hFABP alone or hFABP+IL-6.

Biomarker content was assessed in a first post-op blood sample (0-6 hours post-surgery) for predicting AKI as previously described. The model was adjusted for age (per year), sex, white race, cardiopulmonary bypass time>120 min, non-elective surgery, pre-op estimated GFR, diabetes, hypertension, centre, congestive heart failure, myocardial infarction, preoperative urine albumin to creatinine ratio, and type of surgery (CABG or valve vs. all others). The results are shown in Table 8 below.

TABLE 8

| Adjusted Model | | hFABP | IL-6 | IL-6:IL-10 | hFABP + IL-6:IL-10 | hFABP + IL-6 |
|---|---|---|---|---|---|---|
| Optimal | AUC | 0.85 | 0.80 | 0.79 | 0.85 | 0.85 |
| | Sensitivity | 0.81 | 0.81 | 0.76 | 0.81 | 0.81 |
| | Specificity | 0.82 | 0.73 | 0.74 | 0.83 | 0.81 |

Relevant portions of references referred to herein are incorporated by reference.

The invention claimed is:

1. A method for diagnosing and treating a human at risk of acute kidney injury (AKI) following cardiac surgery comprising detecting in a biological sample from the human a sample value for: (a) the ratio of IL-6 concentration to IL-10 (interleukin-10) concentration and (b) hFABP (heart-type fatty acid binding protein) concentration within 2-4 months pre-operatively—and/or within 3 days post-operatively, wherein when the human is 18 years old or less hFABP is only detected pre-operatively; comparing the sample values to corresponding reference values for the ratio of IL-6 concentration to IL-10 concentration and for hFABP concentration in a control population having the same or similar cardiac surgery and no AKI; determining that the human is at risk of acute kidney injury following cardiac surgery if the sample values are equal to or greater than the corresponding reference values, and treating the human when determined to be at risk of AKI by at least administration of one of furosemide, bicarbonate, desmopressin or estrogen.

2. The method of claim 1, wherein a concentration of IL-6 which is greater than about three times that of IL-10 in the biological sample from the human pre-operatively is indicative of risk of acute kidney injury following cardiac surgery.

3. The method of claim 1, wherein the sample values are obtained within 60 days pre-operatively.

4. The method of claim 1, wherein the human is greater than 18 years old and the ratio of IL-6 concentration to IL-10 concentration is detected pre-operatively or post-operatively and hFABP concentration is detected post-operatively.

5. The method of claim 1, wherein the sample values for the ratio of IL-6 concentration to IL-10 concentration and for hFABP concentration are determined to be at least 20% greater than the corresponding reference values.

6. The method of claim 1, wherein the pre-operative reference value for hFABP is about 3 ng/ml or greater, and the post-operative reference value for hFABP is about 20 ng/mL or greater.

7. The method of claim 1, wherein the pre-operative reference value for IL-6:IL-10 is about 1.8 or greater, or the post-operative reference ratio for IL-6:IL-10 is about 2 or greater.

8. The method of claim 6, wherein the pre-operative reference value for hFABP is about 5 ng/ml or greater, or the post-operative reference value for hFABP is about 40 ng/ml or greater.

9. The method of claim 1, wherein the pre-operative reference value for IL-6:IL-10 is about 2 or greater, or the post-operative reference ratio for IL-6:IL-10 is about 8.5 or greater.

10. The method of claim 1, wherein the sample values for the ratio of IL-6 concentration to IL-10 concentration and hFABP concentration are detected using an immunoassay, or is determined based on a determination of the amount of nucleic acid encoding IL-6, IL-10 and hFABP using a PCR-based technique.

* * * * *